United States Patent [19]

Foulletier

[11] Patent Number: 4,876,406
[45] Date of Patent: Oct. 24, 1989

[54] PROCESS FOR GASEOUS PHASE FLUORINATION OF ALIPHATIC CHLORINATED OR CHLOROFLUORINATED HYDROCARBONS

[75] Inventor: Louis Foulletier, Oullins, France

[73] Assignee: PCUK-Produits Chimiques Ugine Kuhlmann, Courbevoie, France

[21] Appl. No.: 669,404

[22] Filed: Nov. 8, 1984

Related U.S. Application Data

[60] Continuation of Ser. No. 429,081, Sep. 30, 1982, abandoned, which is a division of Ser. No. 324,438, Nov. 24, 1981, abandoned.

[30] Foreign Application Priority Data

Dec. 29, 1980 [FR] France .................................. 80 27662

[51] Int. Cl.$^4$ ....................... C07C 17/20; C07C 17/09
[52] U.S. Cl. ..................................... 570/165; 502/210; 570/168
[58] Field of Search ............... 570/165, 168, 169, 170, 570/175

[56] References Cited

U.S. PATENT DOCUMENTS

| 2,161,984 | 6/1939 | Sweeney et al. | 252/435 |
|---|---|---|---|
| 3,157,707 | 11/1964 | Clark et al. | 252/441 |
| 3,271,299 | 9/1966 | Kearby | 208/114 |
| 3,342,750 | 9/1967 | Kearby | 252/437 |
| 3,591,646 | 7/1971 | Vecchio et al. | 570/168 |
| 3,992,325 | 11/1976 | Knaak | 252/441 |
| 4,219,444 | 8/1980 | Hill et al. | 252/435 |
| 4,444,962 | 4/1984 | McDaniel et al. | 502/210 |

FOREIGN PATENT DOCUMENTS

| 703155 | 2/1965 | Canada | 570/170 |
|---|---|---|---|
| 27138 | 2/1980 | Japan | 502/210 |

*Primary Examiner*—J. E. Evans
*Attorney, Agent, or Firm*—Pennie & Edmonds

[57] ABSTRACT

This invention relates to improved catalysts for gaseous phase fluoridation of aliphatic chlorinated and chlorofluorinated hydrocarbons by hydrofluoric acid. The catalysts comprise chromium salts or oxides complexed with aluminum phosphate and are characterized by a total specific surface area greater than about 200 m$^2$/g, but less than about 1000 m$^2$/g a surface area of pores of 40 to 50 Å in radius above about 5 m$^2$/g, but less than about 150 m$^2$/g, a surface area of pores greater than or equal to 250 Å in radius above about 2 m$^2$/g. but less than about 60 m$^2$/g. This invention also relates to gaseous phase fluoridation processes for chlorinated or chlorofluorinated derivatives utilizing these catalysts in fluidized bed reactors.

9 Claims, No Drawings

PROCESS FOR GASEOUS PHASE FLUORINATION OF ALIPHATIC CHLORINATED OR CHLOROFLUORINATED HYDROCARBONS

This is a continuation of application Ser. No. 429,081, filed 9/30/82, which is a division of application Ser. No. 324,438 filed 11/24/81, both now abandoned.

TECHNICAL FIELD

This invention relates to improved catalysts for gaseous phase fluorination with anhydrous hydrofluoric acid of chlorinated and chlorofluorinated aliphatic hydrocarbons. The catalysts comprise chromium salts or oxides complexed with aluminum phosphate.

This invention also relates to gaseous phase fluorination processes of chlorinated or chlorofluorinated derivatives utilizing these catalysts in fluidized bed reactors.

BACKGROUND OF THE INVENTION

Various catalysts which substitute fluorine atoms for chlorine atoms have been proposed for use in gaseous phase reactions. Frequently, these catalysts are oxides or halides of chromium, aluminum, cobalt, iron, titanium, nickel, copper, palladium or zirconium; which may be used as they are or on various supports.

French Patent No. 720,474 and its Certificate of Addition No. 43,972 teach gaseous phase fluorination of hydrocarbons containing a halogen other than fluorine by metallic halide catalysts.

U.S. Pat. No. 2,210,369 discloses the fluorination of $C_1$ to $C_3$ halohydrocarbons over catalysts having a chromium halide base deposited on coke or active carbon.

French Patent No. 2,000,688 teaches the use of a chromium trifluoride catalyst supported on wood charcoal, petroleum coke, or coal carbon in reactions of chlorine and hydrofluoric acid with tetrachloroethylene.

British Patent No. 896,068 and U.S. Pat. No. 3,157,707 describe catalysts comprising a chromium oxide base deposited on activated alumina. The catalysts are useful in the preparation of fluorinated compounds such as trichlorotrifluoroethane and dichlorotetrafluoroethane from hexachloroethane.

U.S. Pat. No. 3,992,325 discloses the use of a chromium $\gamma$-CrOOH hydroxide-oxide catalysts which is deposited on mineral fluorides as, for example, alkaline-earth fluorides.

U.S. Pat. No. 2,775,313 describes the use of aluminum trifluoride, prepared from gaseous or liquid aluminum trichloride in the fluorination of hexachloroethane formed in situ.

These commonly used catalysts are basically suitable for gaseous phase fluorination of chloroalkanes or chlorofluoroalkanes in fixed bed reactor systems. In fluidized bed reactors, which require regular-shaped particles and homogeneous granulometry, the prior art catalysts are inadequate and inefficient for use in fluorination processes. Simple grinding of the catalysts, followed by sifting for the selection of suitable-sized particles provides irregularly-shaped grains which are not suitable for use in fluidized bed reactors. Consequently, their use leads to a significant loss of the catalyst, which necessitates recharging the reactor at various intervals during the process.

The prior art catalysts often demonstrate at least one of the following disadvantages:
  low rate of conversion of hydrofluoric acid
  low productivity
  low selectivity
  high amounts of asymmetric isomers in the production of trichlorotrifluoroethane and dichlorotetrafluoroethane Known fluorination catalysts, especially those containing aluminum, catalyze dismutation reactions such as:

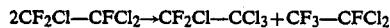

or isomerization reactions such as:

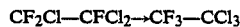

Asymmetric isomers of trichlorotrifluoroethane ($CF_3$—$CCl_3$) and dichlorotetrafluoroethane ($CFCl_2$—$CF_3$) are undesirable in many applications since they are more reactive, and consequently, more unstable than the symmetric derivatives ($CCF_2Cl$—$CFCl_2$ and $CClF_2$—$CClF_2$.)

SUMMARY OF THE INVENTION

All of the disadvantages seen with the known catalysts are remedied by the preparation of the gaseous phase fluorination catalysts of this invention. The catalysts comprise chromium salts or oxides complexes with aluminum phosphate, have an elevated mesoporosity and macroporosity, and are easily shaped.

The applicant has discovered that gaseous phase fluorination catalysts are frequently tainted by the formation of tar on their surfaces and that the use of gaseous phase fluorination catalysts in fluidized bed reactors in advantages since they cause abrasion of the catalyst grains, thus eliminating any attached tar and promoting catalytic activity. The catalyst is uniquely consumed by attrition and there is no need to stop the reaction in order to recharge the reactor with the catalyst.

DETAILED DESCRIPTION OF THE INVENTION

The gaseous phase fluorination catalysts of this invention eliminate the need for supports, such as active carbon, which vary from one lot to another. These catalysts are obtained from synthetic material and have perfectly reproducible characteristics. A further advantage of the catalysts disclosed herein is that by extrusion and granulation, they are easily made into a form suitable for use in a fluidized bed reactor.

The catalysts of this invention comprise a specific surface area which is greater than about 200 $m^2/g$ but less than about 1000 $m^2/g$. The mesoporosity of the gaseous phase fluorination catalysts, defined by a surface area of pores of 40 to 50 Å in radius, should be greater than about 5 $m^2/g$ but less than about 15 $m^2/g$. The macroporosity of the catalysts, defined by a surface area of pores equal to or above 250 Å in radius, should be greater than about 2 $m^2/g$ but less than about 60 $m^2/g$. The amount of chromium in the catalyst should be between about 0.1 to 0.3 atoms/g per liter.

Although aluminum phosphate itself demonstrates low catalytic activity when used in gaseous phase fluorination reactions, its activity is considerably increased when it is complexed with chromium salts or oxides according to this invention.

While the known aluminum-containing catalysts demonstrate strong isomerization activity with regard to trichlorotrifluoroethane and dichlorotetrafluoroethane, their use leads to the formation of very high proportions of asymmetric isomers of these compounds. A totally unexpected result, when the catalysts of this invention are used, is the preferential formation of symmetric isomers.

The catalysts are easily prepared by mixing a chromium salt or oxide, an aluminum salt, phosphoric acid and ammonia in an aqueous solution. Under these conditions, a mixed chromium and aluminum phosphate precipitates. After washing, the precipitate can be easily extruded and granulated.

According to an advantageous embodiment of the invention, a catalyst comprising chromium salts or oxides deposited on aluminum phosphate are prepared by a method which includes the following steps:
(a) adding ammonia to an aqueous solution of an aluminum salt and phosphoric acid;
(b) washing the precipitated aluminum phosphate;
(c) forming the washed aluminum phosphate into pellets by granulation-extrusion;
(d) impregnating the pellets with an aqueous solution of chromium trioxide;
(e) reducing the chromium trioxide with an alcohol;
(f) drying the product with, advantageously, heated air at a temperature of about 150° C.

EXAMPLES

The following examples demonstrate various methods of preparing the catalysts of this invention and uses of the catalysts in various fluorination reactions. The examples are set forth for the purpose of illustration only and are not to be construed as limiting the scope of the invention in any manner.

EXAMPLE 1

218 cm$^3$ of an aqueous solution of ammonia 11N is poured into 1100 cm$^3$ of a solution of 0.6 mole of aluminum chloride and 0.63 mole of phosphoric acid, which is maintained at a temperature between 0° and 150° C. Under strong agitation, a solution of 0.045 mole of chromium sulfate in 300 cm$^3$ of water is poured into the ammonia-aluminum chloride-phosphoric acid mixture. A precipitate is obtained, which is washed twice with one liter of water, and then with one liter of isopropanol. The product is passed into a granulator-extruder, which yields small rods, and is then dried under a vacuum and calcined at 400° C. for 4 hours.

The catalyst obtained has the following characteristics:

| | |
|---|---|
| Density | 0.687 g/cm$^3$ |
| Total Specific Surface Area | 217 m$^2$/g |
| Surface Area of Pores Having a Radius ≧ 250 Å | 2.47 m$^2$/g |
| Surface Area of Pores Having a Radius = 50–250 Å | 92 m$^2$/g |
| Surface Area of Pores Having a Radius = 40–50 Å | 31 m$^2$/g |

The catalyst is advantageously used for the fluorination of trichlorotrifluoroethane in a fluidized bed under the following conditions:

| | |
|---|---|
| Molar Ratio HF/C$_2$Cl$_3$F$_3$ | 0.97/1 |
| Flow Rate | 14.2 moles/h/l |
| Temperature | 405° C. |

The conversion rate of hydrofluoric acid is 82%. The conversion rates of trichlorotrifluoroethane are:
74% into dichlorotetrafluoroethane, containing 71% symmetric isomer
8% into monochloropentafluoroethane

EXAMPLE 2 (COMPARATIVE EXAMPLE USING ONLY ALUMINUM PHOSPHATE)

The catalyst is prepared as in Example 1, except that chromium sulfate is not added to the mixture.

The catalyst obtained has the following characteristics:

| | |
|---|---|
| Density | 0.28 g/cm$^3$ |
| Total Specific Surface Area | 108.2 m$^2$/g |
| Surface Area of Pores Having a Radius ≧ 250 Å | 17 m$^2$/g |
| Surface Area of Pores Having a Radius = 50–250 Å | 34 m$^2$/g |
| Surface Area of Pores Having a Radius = 40–50 | 27 m$^2$/g |

This catalyst is used, under the conditions of Example 1, for the fluorination of trichlorotrifluoroethane in a fluidized bed reactor.

The conversion rate of hydrofluoric acid is only 56%. The conversion rates of trichlorotrifluoroethane are:
65% into dichlorotetrafluoroethane, containing 5% symmetric isomer
1% into monochloropentafluoroethane

EXAMPLE 3

The catalyst of Example 2 is impregnated with a solution of 0.00906 mole of chromium trioxide (CrO$_3$) in 60 cm$^3$ of water. The chromium trioxide is reduced by methanol. Subsequently, the product is dried with heated air at 150° C.

The catalyst of Example 3 is used in the fluorination of trichlorotrifluoroethane in a fluidized bed reactor under the following conditions:

| | |
|---|---|
| Molar Ratio HF/C$_2$Cl$_3$F$_3$ | 1.26/1 |
| Flow Rate | 15.4 moles/h/l |
| Temperature | 411° C. |

The conversion rate of hydrofluoric acid is 67%. The conversion rates of trichlorotrifluoroethane are:
70% into dichlorotetrafluoroethane, containing 47% symmetric isomer
8.3% into monochloropentafluoroethane

I claim:
1. A gaseous phase fluorination process which comprises contacting aliphatic chlorinated or chlorofluorinated hydrocarbons with hydrofluoric acid in the presence of a catalyst in a fluidized bed reactor, said catalyst consisting essentially of a mixed chromium and aluminum phosphate precipitate having:
(a) a specific surface area greater than about 200 m$^2$/g, but less than about 1,000 m$^2$/g,
(b) a surface area of a pores of 40 to 50 Å in radius which is greater than about 5 m$^2$/g, but less than about 150 m$^2$/g,

(c) a surface area of pores equal to or above 250 Å in radius which is greater than about 2 m²/g, but less than about 60 m²/g, and (d) a chromium content between about 0.1 and 3 moles per liter.

2. The process according to claims 1 which further comprises preparing the catalyst by mixing chromium sulfate, aluminum chloride, phosphoric acid and ammonia in aqueous solution until a mixed chromium and aluminum phosphate precipitate is obtained.

3. A gaseous phase fluorination process which consists essentially of contacting aliphatic chlorinated or chlorofluorinated hydrocarbons with hydrofluoric acid in the presence of a catalyst in a fluidized bed reactor, said catalyst consisting essentially of a mixed chromium and aluminum phosphate precipitate having:

(a) a specific surface area greater than about 200 m²/g, but less than about 1,000 m²/g, (b) a surface area of a pores of 40 to 50 Å in radius which is greater than about 5 m²/g, but less than about 150 m²/g, (c) a surface area of pores equal to or above 250 Å in radius which is greater than about 2 m²/g, but less than about 60 m²/g, and (d) a chromium content between about 0.1 and 3 moles per liter.

4. The process according to claim 3 wherein the catalyst is prepared by mixing chromium sulfate, aluminum chloride, phosphoric acid and ammonia in aqueous solution until a mixed chromium and aluminum phosphate precipitate is obtained.

5. A gaseous phase fluorination process for forming symmetric isomers of fluorinated aliphatic hydrocarbons which comprises reacting aliphatic chlorinated or chlorofluorinated hydrocarbons with hydrofluoric acid in the presence of a catalyst in a fluidized bed reactor to form said symmetric isomers, said catalyst consisting essentially of a mixed chromium and aluminum phosphate precipitate having:

(a) a specific surface area greater than about 200 m²/g, but less than about 1,000 m²/g, (b) a surface area of a pores of 40 to 50 Å in radius which is greater than about 5 m²/g, but less than about 150 m²/g, (c) a surface area of pores equal to or above 250 Å in radius which is greater than about 2 m²/g, but less than about 60 m²/g, and (d) a chromium content between about 0.1 and 3 moles per liter.

6. The process according to claim 5 which further comprises preparing the catalyst by mixing chromium sulfate, aluminum chloride, phosphoric acid and ammonia in aqueous solution until a mixed chromium and aluminum phosphate precipitate is obtained.

7. A gaseous phase fluorination process for forming symmetric isomers of fluorinated aliphatic hydrocarbons which consists essentially of reacting aliphatic chlorinated or chlorofluorinated hydrocarbons with hydrofluoric acid in the presence of a catalyst in a fluidized bed reactor to form said symmetric isomers, said catalyst consisting essentially of a mixed chromium and aluminum phosphate precipitate having:

(a) a specific surface area greater than about 200 m²/g, but less than about 1,000 m²/g, (b) a surface area of a pores of 40 to 50Å in radius which is greater than about 5 m²/g, but less than about 150 m²/g, (c) a surface area of pores equal to or above 250 Å in radius which is greater than about 2 m²/g, but less than about 60 m²/g, and (d) a chromium content between about 0.1 and 3 moles per liter.

8. The process according to claim 7 wherein the catalyst is prepared by mixing chromium sulfate, aluminum chloride, phosphoric acid and ammonia in aqueous solution until a mixed chromium and aluminum phosphate precipitate is obtained.

9. A gaseous phase fluorination process for forming symmetric isomers of fluorinated aliphatic hydrocarbons which consists essentially of preparing a catalyst of a mixed chromium and aluminum phosphate precipitate by mixing chromium sulfate, aluminum chloride, phosphoric acid and ammonia in aqueous solution; said catalyst having:

(a) a specific surface area greater than about 200 m²/g, but less than about 1,000 m²/g, (b) a surface area of a pore size of 40 to 50 Å in radius which is greater than about 5 m²/g but less than about 150 m²/g, (c) a surface area of pores equal to or above 250 Å in radius which is greater than about 2 m²/g, but less than about 60 m²/g, and (d) a chromium content between about 0.1 and 3 moles per liter; and recovering said mixed duromium and aluminum precipitate; and reacting aliphatic chlorinated or chlorofluorinated hydrocarbons with hydrofluoric acid in the presence of said catalyst in a fluidized bed reactor.

* * * * *

UNITED STATES PATENT AND TRADEMARK OFFICE
CERTIFICATE OF CORRECTION

PATENT NO. : 4,876,406
DATED : October 24, 1989
INVENTOR(S) : Foulletier

It is certified that error appears in the above-identified patent and that said Letters Patent is hereby corrected as shown below:

Column 3, line 43, "150° C" should read -- 15° C --.

Signed and Sealed this

Twenty-second Day of January, 1991

Attest:

HARRY F. MANBECK, JR.

*Attesting Officer*     *Commissioner of Patents and Trademarks*